(12) United States Patent
Krummen

(10) Patent No.: US 8,632,726 B2
(45) Date of Patent: Jan. 21, 2014

(54) DEVICE AND METHOD FOR PRODUCING CARBON DIOXIDE, NITRIDE AND/OR SULFUR DIOXIDE FROM A SAMPLE

(75) Inventor: Michael Krummen, Bad Zwischenahn (DE)

(73) Assignee: Thermo Fischer Scientific (Bremen) GmbH, Bremen (DE)

( * ) Notice: Subject to any disclaimer, the term of this patent is extended or adjusted under 35 U.S.C. 154(b) by 137 days.

(21) Appl. No.: 12/935,872

(22) PCT Filed: Mar. 25, 2009

(86) PCT No.: PCT/EP2009/002152
§ 371 (c)(1),
(2), (4) Date: Sep. 30, 2010

(87) PCT Pub. No.: WO2009/121506
PCT Pub. Date: Oct. 8, 2009

(65) Prior Publication Data
US 2011/0027161 A1   Feb. 3, 2011

(30) Foreign Application Priority Data
Mar. 31, 2008 (DE) .......................... 10 2008 016 583

(51) Int. Cl.
*G01N 31/10* (2006.01)
*G01N 31/12* (2006.01)
*H01J 49/00* (2006.01)

(52) U.S. Cl.
USPC ............. 422/80; 250/281; 250/282; 250/288; 422/78; 422/94; 422/129; 436/106; 436/119; 436/122; 436/139; 436/155; 436/159; 436/160; 436/161; 436/173; 436/174; 436/181

(58) Field of Classification Search
USPC .......... 250/281–282, 288; 436/106, 119, 122, 436/139, 155, 159–161, 173–174, 181; 422/78, 80, 94, 129
See application file for complete search history.

(56) References Cited

U.S. PATENT DOCUMENTS 3,776,695 A * 12/1973 Peterson .......................... 436/59
3,811,838 A *  5/1974 Saito et al. ...................... 436/59
3,840,341 A * 10/1974 Rogers .......................... 436/146
(Continued)

FOREIGN PATENT DOCUMENTS

DE            33 06 732 A1    8/1984

OTHER PUBLICATIONS

Palhol, F. et al, Analytica Chimica Acta 2004, 510, 1-8.*
(Continued)

*Primary Examiner* — Arlen Soderquist
(74) *Attorney, Agent, or Firm* — Charles B. Katz; Nicholas Cairns

(57) ABSTRACT

The invention relates to a device for producing $CO_2$, $N_2$ and/or $SO_2$ from a sample for a quantitative analysis of the sample, comprising a reactor structure and metals acting in an oxidizing manner or metal oxides in the reactor. According to the invention, the reactor structure has at least two zones through which the sample can flow, which is to say a first zone with reactor metal and reservoir metal, or only reactor metal, and following the first zone, a second zone with reactor metal and reservoir metal, or only reservoir metal, wherein both metals can form oxides, and wherein the ratio of the reactor metal to the reservoir metal in the first zone is greater than in the second zone.

14 Claims, 3 Drawing Sheets

(56) References Cited

U.S. PATENT DOCUMENTS

| | | | |
|---|---|---|---|
| 3,861,874 A * | 1/1975 | Krc | 436/149 |
| 4,040,789 A * | 8/1977 | Voss et al. | 436/114 |
| 4,234,315 A * | 11/1980 | Scott | 436/115 |
| 4,285,699 A * | 8/1981 | Itoh | 436/114 |
| 4,293,308 A * | 10/1981 | Sisti et al. | 436/115 |
| 4,332,591 A * | 6/1982 | Oi et al. | 436/114 |
| 4,401,763 A * | 8/1983 | Itoh | 436/115 |
| 4,916,313 A * | 4/1990 | Hall et al. | 250/282 |
| 5,012,052 A * | 4/1991 | Hayes | 250/288 |
| 5,314,827 A * | 5/1994 | Schmidt et al. | 436/106 |
| 5,432,344 A * | 7/1995 | Brand | 250/288 |
| 5,766,954 A * | 6/1998 | Freedman et al. | 436/144 |
| 5,783,741 A * | 7/1998 | Ellis et al. | 73/23.39 |
| 5,976,890 A * | 11/1999 | Gehre et al. | 436/144 |
| 6,031,228 A * | 2/2000 | Abramson | 250/288 |
| 7,976,780 B2 * | 7/2011 | Elrod et al. | 422/78 |
| 2002/0060288 A1 * | 5/2002 | Hughey et al. | 250/281 |
| 2003/0226394 A1 * | 12/2003 | Hilkert et al. | 73/23.39 |
| 2005/0266580 A1 * | 12/2005 | Italiano et al. | 436/106 |
| 2007/0284523 A1 * | 12/2007 | May et al. | 250/288 |
| 2010/0212398 A1 * | 8/2010 | Krummen et al. | 73/23.37 |

OTHER PUBLICATIONS

Calderone, G. et al, Journal of Agricultural and Food Chemistry 2004, 52, 5902-5906.*

Ellis et al., "Analytical improvements in irm-GC/MS analyses: Advanced techniques in tube furnace design and sample preparation," Organic Geochemistry, 29, (5-7), 1998, pp. 1101-1117.

* cited by examiner

DEVICE AND METHOD FOR PRODUCING CARBON DIOXIDE, NITRIDE AND/OR SULFUR DIOXIDE FROM A SAMPLE

BACKGROUND OF THE INVENTION

The invention relates to a device and a method for forming $CO_2$, $N_2$ and/or $SO_2$ from a sample for quantitative analysis of the sample, having a reactor structure and metals or metal oxides acting in an oxidizing manner on carbon in the reactor structure. Preferably, the sample is an organic sample, a derivative of an organic sample or generally a GC-handleable substance. In addition, the invention relates to a use of the device.

Reference is made to the disclosure in U.S. Pat. No. 5,432,344 and to the publication DE 42 32 301 A of the associated first German filing. These documents are incorporated in entirety in the disclosure of the present invention. The documents concern an appliance for isotope ratio analysis, having a gas chromatograph, a combustion furnace and a mass spectrometer. A sample is resolved in the gas chromatograph into single gaseous components which are intended to be reduced in the combustion furnace to simple gases. The latter must be suitable for analysis in the mass spectrometer. In particular, the formation of $CO_2$ and/or $N_2$ is intended or possible. The formation of $SO_2$ from sulfur-containing compounds is also conceivable. The gas coming from the gas chromatograph flows through the combustion furnace and is oxidized in the course of this. In the combustion furnace, as an aid for the oxidation, nickel oxide is provided, optionally in combination with copper oxide.

The combustion furnace has only a restricted service life. After a certain amount of gas has passed through, the metal oxide present in the combustion furnace is consumed to the extent that the measurement results are no longer satisfactory. Reoxidation of the metal is necessary. Extension of the service life or of the reoxidation intervals is sought.

Nitrogen oxides are also formed from the sample in the combustion furnace. These nitrogen oxides are customarily converted in a downstream reduction reactor to $N_2$. The additional reduction reactor increases the complexity of apparatus of the overall system.

SUMMARY OF THE INVENTION

It is an object of the present invention to provide a device having an extended service life and/or a simpler structure.

The device according to the invention is characterized in that the reactor structure has at least two zones through which the sample can flow, namely a first zone having reactor metal and reservoir metal or only reactor metal and a second zone which follows the first zone having reactor metal and reservoir metal or only reservoir metal, wherein both metals can form oxides, and wherein the ratio reactor metal/reservoir metal in the first zone is greater than in the second zone. Said ratio relates to the surface areas of the metals. The sample or components thereof flowing through the reactor structure come into contact with the metallic surfaces and react there. The subject matter of the invention also includes the following alternatives:

a) in the first zone there is only reactor metal, in the second zone only reservoir metal;
b) in the first zone there is only reactor metal, in the second zone reactor metal and reservoir metal;
c) in the first zone there is reactor metal and reservoir metal, in the second zone only reservoir metal.

Reactor metal and reservoir metal are preferably matched to one another in such a manner that the reservoir metal can deliver oxides to the reactor metal. Customarily the gas flows through the reactor structure continuously in the long term. However, it is also possible to have only temporary gas flow through the reactor structure.

Reactor metal and/or reservoir metal are present in pure form, as alloy or as oxides. For preparing for the first operation of the device, the reactor metal and reservoir metal present in pure form are oxidized, for example, by oxygen feed. The oxygen bound in this manner is of critical importance for the function of the device, namely for forming $CO_2$ and/or $N_2$.

The division of the reactor structure into at least two zones has the following effects:

After starting, $CO_2$ is formed in the first zone, in further operations, $CO_2$ and CO. In the second zone the resultant CO is oxidized to $CO_2$. At the same time, few or no unwanted byproducts such as, e.g. nitrogen oxides, are formed by the structure described. Rather, $N_2$ is directly formed. $CO_2$ and $N_2$ (or $SO_2$) can be studied with respect to their isotope ratios in a subsequent mass spectrometer. By avoiding CO and other unwanted byproducts, the measurements are not adversely affected by molecules having the same or similar masses.

As reactor metal, preferably nickel or nickel oxide is provided, as reservoir metal, preferably copper or copper oxide. In experiments to date, the best results have been achieved using these two metals.

Advantageously, the ratio reactor metal/reservoir metal in the second zone is about 1. In particular, said ratio is between 0.7 and 1.5.

According to a further concept of the invention, the ratio reactor metal/reservoir metal in the first zone is greater than 1.5, preferably 2 or more. In particular, said ratio is 5 or more. A significantly greater ratio of reactor metal to reservoir metal in the first zone relative to the second zone is sought.

According to a further concept of the invention, at least twice as much reservoir metal is provided in the first zone as in the second zone, preferably eight times as much. As already stated above, the ratios relate to the active surfaces of the metals or metal oxides in the two zones.

Advantageously, the reactor metal is one of the following metals or alloy thereof or oxide thereof:
nickel, copper, cadmium, iron, vanadium, manganese, chromium, palladium, silver, platinum.

Advantageously, the reservoir metal is one of the following metals or alloy thereof or oxide thereof:
tin, lead, copper, silver, iron, mercury.

Corresponding to the arrangement of the metals in the Periodic Table of the Elements, the reservoir metal should be nobler as far as possible than the reactor metal. The above-mentioned metals as examples of the reservoir metal are particularly advantageous in combination with nickel as reactor metal.

According to a further concept of the invention, in the first zone, a tube is provided in which at least the surface of an inner wall is made of the reactor metal, wherein in addition at least the reservoir metal of the first zone is arranged in the tube. The reservoir metal can be present in the tube, for example in the form of wires, swarf or powder. In addition, further reactor metal can be present in the tube, for example likewise in the form of wires, swarf or powder.

According to a further concept of the invention, wires made of reactor metal and reservoir metal are inserted into the tube of the first zone. In addition, the second zone is formed by a projection of said wires beyond the tube. This embodiment is particularly simple in the structure. What are required are only the tube having the surface made of reactor metal, a wire made of reactor metal and a wire made of reservoir metal, wherein said wires are longer than the tube and project from the tube as a "plume" in the direction of flow. The whole can be surrounded by an enclosing furnace tube, for example made of a ceramic material.

According to the invention, a tube for receiving reactor metal and reservoir metal can be provided in the first zone and a tube for receiving reactor metal and reservoir metal can be provided in the second zone, wherein the two tubes can be separated from one another or be successive sections of one and the same tube. Metal swarf, wires or powder can be introduced, for example, into the tubes or the tube. In the case of the arrangement of two successive tubes, a cold zone can also be present inbetween, as in conventional appliances having an oxidation reactor and reduction reactor.

According to a further concept of the invention, the first zone is longer in the direction of flow than the second zone, in particular by the factor 2 to 15, preferably by the factor 4 to 8.

According to a further concept of the invention, the second zone is cooler or is less heated than the first zone, namely having chiefly room temperature to 800° C. in the second zone and chiefly 800° C. to 1200° C. in the first zone. Temperatures having a peak range of 900° C. to 1100° C. in the first zone and decreasing starting therefrom in the subsequent second zone are expedient. In principle, the invention also functions with equal temperatures in the two zones. The temperatures should then, however, be preferably in said hotter range.

The device according to the invention is preferably part of a larger appliance for the analysis of said, in particular organic, samples, namely in combination with a mass spectrometer, in particular for the analysis of isotope ratios. This larger appliance can also include a gas chromatograph, as already described in U.S. Pat. No. 5,432,344.

The invention further relates to the use of the device according to the invention for a spectrometric analysis, in particular optical analysis, or mass spectrometric analysis, preferably for determining isotope ratios. However, the device is also advantageously useable for relatively simple quantitative analyses of an organic sample with formation of $CO_2$ and/or $N_2$ and/or $SO_2$.

BRIEF DESCRIPTION OF THE DRAWINGS

Further features of the invention and also the method according to the invention result from the description in general and from the claims. Advantageous embodiments of the invention will be described in more detail hereinafter with reference to drawings. In the drawings:

DETAILED DESCRIPTION OF EMBODIMENTS OF INVENTION

Figure 1:
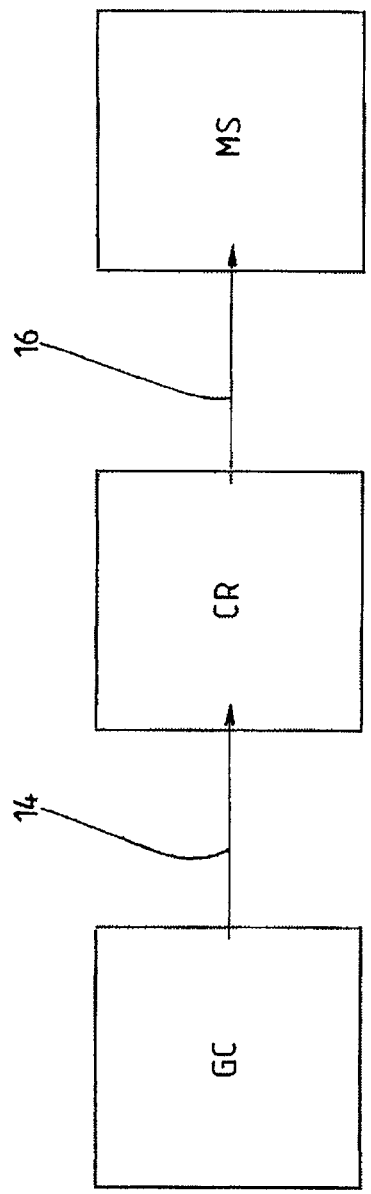
FIG. 1 shows an outline sketch which shows the arrangement of a device according to the invention in an overall system having gas chromatograph and mass spectrometer.

For preparing a mass spectrometric analysis, an organic sample is resolved with respect to time in a gas chromatograph GC. The complex gases pass from the GC into a combustion reactor CR and are there converted or oxidized with supply of heat and in the presence of metal oxides to simple gases. What is sought is in particular a conversion to $CO_2$ and $N_2$. The resultant simple gases are fed for analysis to a mass spectrometer MS. The representation in FIG. 1 is highly simplified. What are not shown here are the further components of such an appliance which are familiar to those skilled in the art and are also possible here, as are shown, for example, in U.S. Pat. No. 5,432,344 and also the structure of the mass spectrometer MS with inlet system, ion source, analyzer, detector and data system. The mass spectrometer is preferably provided for isotope ratio analysis. However, the invention is also useable in connection with other quantitative analyses in which high accuracy and complete conversion of the sample to simple gases is of importance.

The structure and function of the combustion reactor CR are of particular interest. According to FIG. 2, a ceramic pipe 10 is arranged in a reactor housing that is not shown, into which a nickel tube 11 is inserted. In the nickel tube 11 are arranged a nickel wire 12 and a copper wire 13.

A feed line 14 is inserted into the ceramic pipe 10 in such a manner that gas can flow into the nickel tube 11 from the feed line 14 without a bypass stream. Gas streams outside the nickel tube 11 must be avoided as far as possible.

The wires 12, 13 end on the side of the feed line 14 flush with the nickel tube 11 and on the other side extend beyond the nickel tube 11 with a short projection 15.

The ceramic pipe 10 extends on the side of the feed line 14 not only over the transition between feed line 14 and nickel tube 11 and on the opposite side further markedly beyond the projection 15 up to a line 16. Around the ceramic pipe 10 is provided a heater 17, the axial position and length of which approximately corresponds to the nickel tube 11 and can alternatively be somewhat shorter or longer. By means of the heater 17, a hot zone 18 is defined in the ceramic pipe 10. Subsequently thereto, in the region of the projection 15 there results a zone 19 which is colder in comparison. The zones 18, 19 can also be designated first and second zones.

Figure 2:
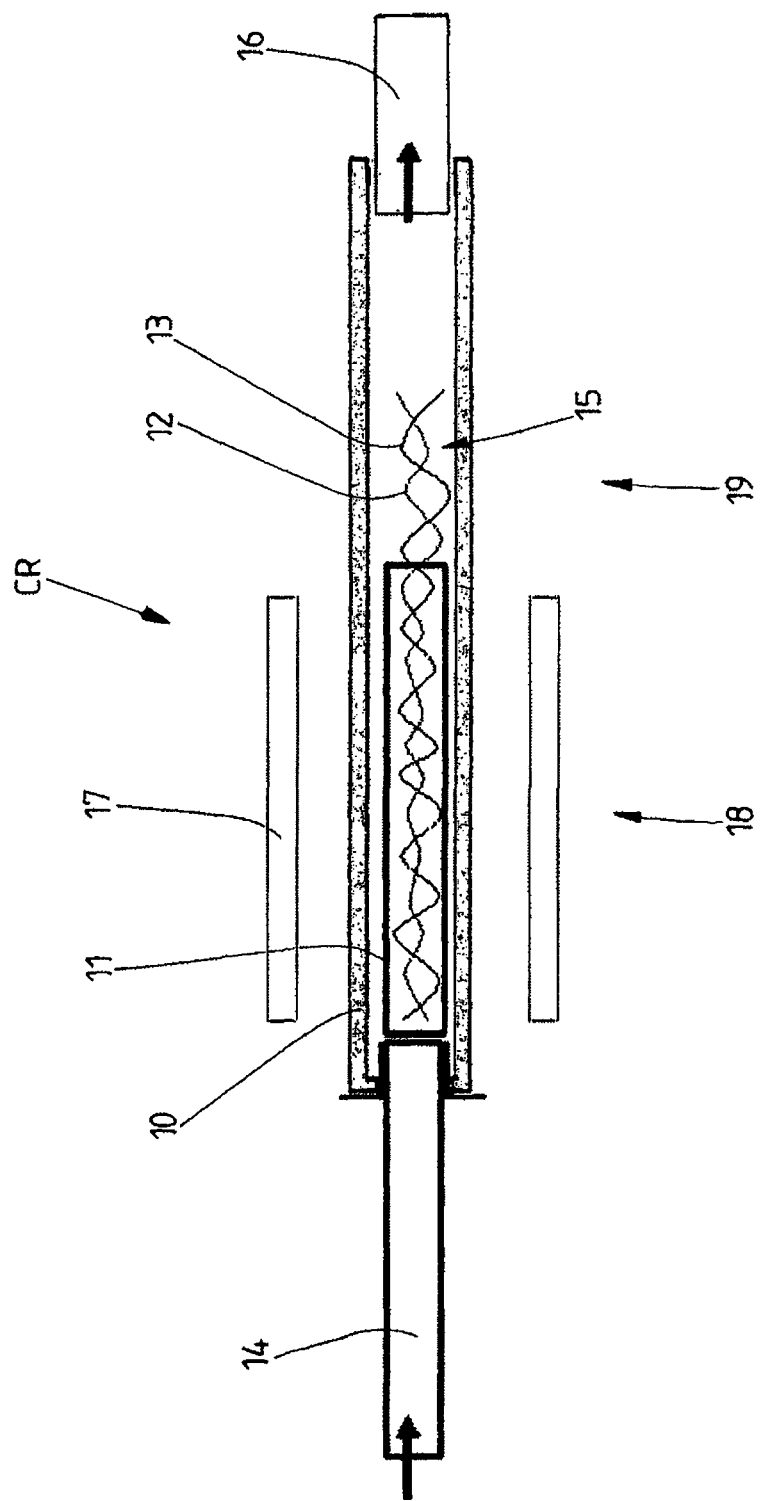
FIG. 2 shows a device according to the invention in longitudinal section.

In the present case, the ceramic pipe has an inner diameter of 0.8 mm and a length of about 40 cm. The nickel tube 11 sits—not as shown in FIG. 2—as tightly as possible in the ceramic pipe 10 and extends over about 20 cm with an inner diameter of 0.5 mm.

The wires 12, 13 extend in axial direction of the pipe 10 over about 25 cm and each have a diameter of about 0.125 mm. The projection 15 beyond the nickel tube 11 is about 5 cm.

Said dimensions correspond to an exemplary embodiment tested in practice. In fact, the size data can vary within wide limits without the function according to the invention being significantly restricted.

An additional gas can also be fed to the gas stream coming from the GC in order to improve the oxidation or to extend the service life. Possible additions are, e.g., air or small amounts of oxygen. A typical carrier gas is helium.

The active surface area of the nickel tube 11 is about 350 $mm^2$. The surface area of the wires 12, 13 is in each case about 100 $mm^2$. Thereof in each case about 20 $mm^2$ extend outside the nickel tube 11, that is to say in the colder zone 19.

Figure 3:
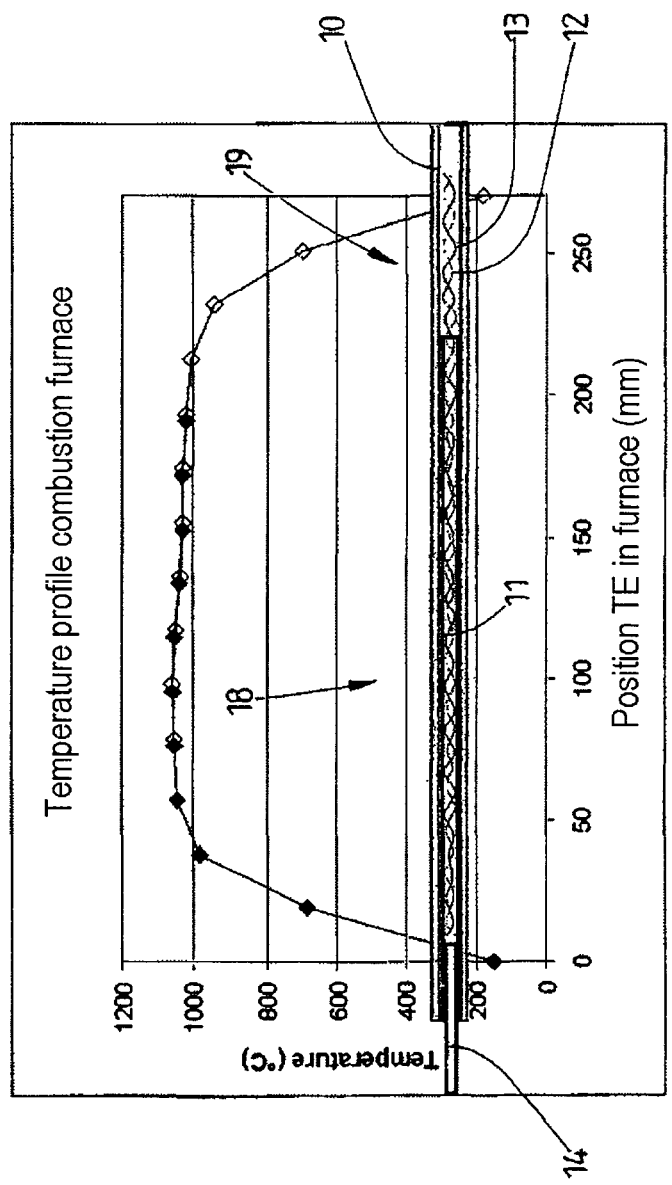
FIG. 3 shows the device according to the invention in longitudinal section with associated temperature profile.

FIG. 3 shows a temperature profile along the two zones 18, 19 and along the ceramic pipe 10. In the region of the nickel tube 11, the temperature first increases steeply and is predominantly 900° C. to 1100° C. In the region of the projection 15 (colder zone 19) the temperature falls sharply and is there predominantly between 900° C. and 200° C.

The various states of the reactor will be described hereinafter:

1. The process proceeds from a reactor in which nickel and copper are present in non-oxidized form. Before measurement the metals are oxidized by feeding oxygen and heat. Metal oxides form according to the following reaction equations:

$$\text{(at 600-650° C.) } 2Cu+O_2 \rightleftharpoons 2CuO \text{ (copper(II) oxide)} \quad \text{A.}$$

$$(>800° C.) \; CuO+Cu \rightleftharpoons Cu_2O \text{ (copper(I) oxide)} \quad \text{B.}$$

and/or $$4CuO \rightleftharpoons 2Cu_2O+O_2 \text{ (copper(I) oxide)}$$

$$2Ni+O_2 \rightleftharpoons 2NiO \text{ (nickel(II) oxide)} \quad \text{C.}$$

The same reactions proceed later during regeneration or reoxidation of the reactor.

2. During measurement a gas stream is conducted through the reactor and simple gases, namely, in particular $CO_2$ and $N_2$, are formed in the reactor from the gases of the organic sample. Oxygen atoms are withdrawn from the metal oxides in the course of this. The reaction or combustion of the compound under study to form $CO_2$ or $N_2$ preferably proceeds on nickel (II) oxide:

$$CH_4+4NiO \rightleftharpoons CO_2+4H_2O+4Ni \quad \text{A.}$$

(usual desired reaction).

The nickel formed in this case is regenerated to nickel oxide by the copper oxide as oxygen donor. The service life of the reactor increases thereby.

If the reactor is consumed minimally, i.e. all of the nickel atoms on the reactor surface are no longer oxidized, it can occur that the combustion of carbonaceous substances to form $CO_2$ no longer proceeds completely. The nickel can also withdraw an oxygen from the $CO_2$:

$$2CH_4+7NiO \rightleftharpoons CO_2+CO+4H_2O+7Ni \quad \text{B.}$$

(incomplete reaction in used reactor).

$$CO_2+Ni \rightleftharpoons CO+NiO \quad \text{C.}$$

(equilibrium reaction which can be shifted depending on the nickel fraction).

Firstly, 100% conversion to $CO_2$ is thereby no longer possible and secondly the CO (m/z 30) formed severely interferes with the delta measurements of $N_2$ ($^{15}N/^{14}N$), and so relevant data can no longer be measured.

By means the nickel-copper plume 15 projecting beyond the nickel tube 11, the CO leaving the hot first zone 18 can be oxidized by the nickel oxide or copper oxide to $CO_2$. The nickel wire situated in the plume 15, in the case of appearance of consumption, owing to its small amount compared with the nickel tube 11, has no affinity to the $CO_2$ to withdraw an oxygen. The above equilibrium reaction C. is strongly shifted to the side of $CO_2$. The nickel wire, however, is advantageous in order to both promote the reaction, and also to minimize the "$O_2$ bleeding" of the copper wire at the temperatures in question.

3. Generally, during the measurement the following exemplary and typical but not comprehensive reaction equations are used as a starting point:

A. Conversion by Nickel $$C_nH_xR_y+zNiO \rightleftharpoons aCO_2+bH_2O+cR_yO_m+dNi$$

$$(CH_4+4NiO \rightleftharpoons CO_2+2H_2O+4Ni \text{ (at 900° C.-1200° C.)})$$

$$(C_8H_{10}N_4O_2+19NiO \rightleftharpoons 8CO_2+5H_2O+2N_2+19Ni \text{ (at 900° C.-1200° C.)})$$

(caffeine)

B. Conversion by Copper $$C_nH_xR_y+zCu_2O \rightleftharpoons aCO_2+bH_2O+cR_yO_m+dCuO+eCu$$

$$(CH_4+4Cu_2O \rightleftharpoons CO_2+2H_2O+4CuO+4Cu \text{ (at 900° C.-1100° C.)})$$

$$(CO+Cu_2O \rightleftharpoons CO_2+2Cu)$$

$$(CO+2CuO \rightleftharpoons CO_2+Cu_2O)$$

C. Internal Regeneration of the Nickel by Copper $$Ni+Cu_2O \rightleftharpoons NiO+2Cu$$

$$Ni+CuO \rightleftharpoons NiO+Cu$$

LIST OF REFERENCE SIGNS

10 ceramic pipe
11 nickel tube
12 nickel wire
13 copper wire
14 feed line
15 projection/plume
16 line
17 heater
18 hot zone (first zone)
19 colder zone (second zone)
CR combustion reactor
GC gas chromatograph
MS mass spectrometer

The invention claimed is:

1. A device for forming at least one of $CO_2$, $N_2$ and $SO_2$ from a sample for quantitative analysis of the sample, comprising:
   a heatable reactor structure including a first zone having one of solely reactor metal or a combination of reactor metal and reservoir metal and a second zone having one of solely reservoir metal or a combination of reservoir metal and reactor metal;
   wherein both the reactor and reservoir metals can form oxides;
   wherein a ratio defined by the surface area of the reactor metal to the reservoir metal is greater in the first zone relative to in the second zone; and
   further comprising a tube located in the first zone having reactor metal disposed on the inner surface thereof and wherein reservoir metal is arranged in the tube.

2. The device as claimed in claim 1, wherein the ratio in the second zone is about 1.

3. The device as claimed in claim 1, wherein the ratio in the first zone is greater than 1.5.

4. The device as claimed in claim 3, wherein the ratio in the first zone is at least 5.

5. The device as claimed in claim 1 wherein the surface area of reservoir metal in the first zone is at least twice the surface area of reservoir metal in the second zone.

6. The device as claimed in claim 1, wherein the reactor metal is selected from one of the following metals or alloy thereof or oxide thereof:
   nickel, copper, cadmium, iron, vanadium, manganese, chromium, palladium, silver, and platinum.

7. The device as claimed in claim 1, wherein the reservoir metal is selected from one of the following metals or alloy thereof or oxide thereof:
   tin, lead, copper, silver, iron, and mercury.

8. The device as claimed in claim 1, including wires of reactor metal and reservoir metal inserted into the tube and projecting beyond the end of the tube into the second zone.

9. The device as claimed in claim 1, further comprising a second tube located in the second zone for receiving reactor metal and reservoir metal.

10. The device as claimed in claim 1, wherein the first zone is at least twice as long in the direction of flow than the second zone.

11. The device as claimed in claim 1, wherein during operation of the device the temperature is maintained between room temperature to 800° C. in the second zone and 800° C. to 1200° C. in the first zone, the temperature in the first zone being higher than the temperature in the second zone.

12. The device as claimed in claim 1, further comprising an isotope mass spectrometer positioned to analyze gases emitted from the reactor structure.

13. A device for forming at least one of $CO_2$, $N_2$ and $SO_2$ from a sample for quantitative analysis of the sample, comprising:
   a heatable reactor structure including a first zone having one of solely reactor metal or a combination of reactor metal and reservoir metal and a second zone having one of solely reservoir metal or a combination of reservoir metal and reactor metal;
   wherein both the reactor and reservoir metals can form oxides;
   wherein a ratio defined by the surface area of the reactor metal to the reservoir metal is greater in the first zone relative to in the second zone; and
   wherein the surface area of reservoir metal in the first zone is at least twice the surface area of reservoir metal in the second zone.

14. A device for forming at least one of $CO_2$, $N_2$ and $SO_2$ from a sample for quantitative analysis of the sample, comprising:
   a heatable reactor structure including a first zone having one of solely reactor metal or a combination of reactor metal and reservoir metal and a second zone having one of solely reservoir metal or a combination of reservoir metal and reactor metal;
   wherein both the reactor and reservoir metals can form oxides;
   wherein a ratio defined by the surface area of the reactor metal to the reservoir metal is greater in the first zone relative to in the second zone; and
   wherein the first zone is at least twice as long in the direction of flow than the second zone.

* * * * *